(12) United States Patent
Rodriguez et al.

(10) Patent No.: US 10,175,227 B2
(45) Date of Patent: Jan. 8, 2019

(54) GAS SENSOR MODULE

(71) Applicants: Steven A. Rodriguez, Seattle, WA (US); Stephen M. Bailey, Shoreline, WA (US); David A. Herrin, Seattle, WA (US); Gordon W. Lam, Renton, WA (US)

(72) Inventors: Steven A. Rodriguez, Seattle, WA (US); Stephen M. Bailey, Shoreline, WA (US); David A. Herrin, Seattle, WA (US); Gordon W. Lam, Renton, WA (US)

(73) Assignee: GM NAMEPLATE, INC., Seattle, WA (US)

(*) Notice: Subject to any disclaimer, the term of this patent is extended or adjusted under 35 U.S.C. 154(b) by 414 days.

(21) Appl. No.: 14/717,833

(22) Filed: May 20, 2015

(65) Prior Publication Data

US 2016/0341715 A1 Nov. 24, 2016

(51) Int. Cl.
| A61B 5/00 | (2006.01) |
| A61B 5/08 | (2006.01) |
| G01N 33/497 | (2006.01) |
| A61B 5/097 | (2006.01) |

(52) U.S. Cl.
CPC ......... *G01N 33/497* (2013.01); *A61B 5/082* (2013.01); *A61B 5/097* (2013.01); *G01N 2033/4975* (2013.01)

(58) Field of Classification Search
CPC ................ A61B 5/082; A61B 5/097
See application file for complete search history.

(56) References Cited

U.S. PATENT DOCUMENTS

| 5,697,326 A | 12/1997 | Mottram et al. |
| 5,811,662 A | 9/1998 | Williams et al. |
| 6,609,068 B2 | 8/2003 | Cranley et al. |
| 7,017,389 B2 | 3/2006 | Gouma |
| 7,872,324 B2 | 1/2011 | Kim et al. |
| 7,955,562 B2 | 6/2011 | Hong et al. |
| 8,281,642 B2 | 10/2012 | Lee et al. |
| 8,330,169 B2 | 12/2012 | Liu et al. |
| 2003/0217586 A1 | 11/2003 | Gouma |
| 2005/0267329 A1* | 12/2005 | Konstorum ........ A61B 1/00039 600/112 |
| 2006/0277974 A1 | 12/2006 | Gouma et al. |
| 2009/0218235 A1 | 9/2009 | McDonald et al. |
| 2010/0147684 A1 | 6/2010 | Park et al. |
| 2010/0198521 A1 | 8/2010 | Haick |
| 2011/0061446 A1 | 3/2011 | Gouma et al. |
| 2011/0317739 A1 | 12/2011 | Cole et al. |
| 2012/0042713 A1 | 2/2012 | Kim et al. |
| 2014/0371619 A1* | 12/2014 | Rodriguez ............ A61B 5/082 600/532 |

FOREIGN PATENT DOCUMENTS

WO 2009/013754 A1 1/2009

* cited by examiner

*Primary Examiner* — Christian Jang
(74) *Attorney, Agent, or Firm* — Christensen O'Connor Johnson Kindness PLLC

(57) ABSTRACT

A sensor module includes a substrate with a slot formed therein. A sensor is mounted to the substrate and spans the slot. A first cover is disposed on a first side of the substrate and covers at least a portion of the slot. The first cover comprises a first aperture and a second aperture in fluid communication with the slot. The sensor is disposed between the first and second apertures.

8 Claims, 17 Drawing Sheets

GAS SENSOR MODULE

BACKGROUND

Exhaled human breath typically comprises approximately 78% nitrogen, 15-18% oxygen, and 4-6% carbon dioxide. The remaining small fraction of exhaled breath generally consists of saturated water vapor and trace levels of more than 1000 volatile organic compounds (VOCs) with concentrations ranging from parts per trillion (pptv) to parts per million (ppmv).

The specific composition of a person's breath can indicate various health conditions. For example, acetone is a VOC in exhaled human breath that can indicate diabetes, heart disease, epilepsy, and other conditions. A person who is in a state of ketosis will have an increased breath concentration of acetone resulting from the body's production of ketone bodies. Acetone is also produced by ketosis resulting from a restricted calorie weight loss and/or exercise program. This acetone production is the result of metabolism of fat. Hence, a breath acetone content measurement can be used as an indication of a medical condition or of fat burning during a diet and/or program to show the effectiveness of the program.

Sensors such as those for detecting acetone in breath samples can be particularly sensitive to the manner in which the sensor is exposed to the sample being tested. While repeatable and accurate results can be obtained in a lab setting by exposing the sensors to a sample in a controlled manner, it is often desirable to analyze a breath sample outside of a lab setting.

Consumer devices and/or portable devices for testing breath samples are typically used outside of a controlled laboratory setting. Such devices generally take a live breath sample and expose the sensor directly to the exhaled human breath, resulting in readings that are neither repeatable nor accurate. Collecting live breath samples, particularly from multiple subjects, causes factors to vary that can otherwise be held relatively constant in the lab gas setup described above. These factors include velocity of exhaled breath, dynamic vapor pressure, duration of exhalation, total volume and individual size of exhaled droplets, and variable oxygen and acetone concentrations that are dependent on which part of the exhaled breath is sampled from (i.e. mouth air, deep lung air, or somewhere in between). Collectively and individually, these variables contribute to poor repeatability and inaccurate measurements.

Known sensors also suffer from designs that inhibit accuracy and repeatability, even when exposed to a controlled, consistent flow of a breath sample. One example of a known acetone sensor 600, shown in FIG. 18, includes tungsten trioxide ($WO_3$) disposed on an alumina or anodic aluminum oxide (AAO) substrate. This and similar sensors have typically been packaged in cylindrical leaded components, such as a standard TO-5 header 602, like the one shown in FIG. 16. While TO-5 and similar headers are readily available, they are expensive, even at high manufacturing volumes. In addition, gas sensors housed in a TO type header are typically exposed to an air sample via diffusion, either through a mesh screen 604 or a hole in the case. As a result, such sensors are typically not well-suited for applications involving a sample having a controlled mass flow.

Acetone sensors are useful for detecting various health conditions and/or for monitoring the efficacy of diet and exercise programs. The acetone level for diet and exercise is lower than that caused by diabetes. Accordingly, a more sensitive, accurate, and repeatable sensor is required in order to monitor increased acetone levels caused by diet and exercise.

The present disclosure is directed to a breath capture and sampling system that captures a breath sample and provides it to a sensor in a manner that produces accurate and repeatable detection of various breath components. Although the described embodiment is directed toward the detection of acetone in a breath sample, it will be appreciated that alternate embodiments are possible wherein other sample components are sensed, and such embodiments should be considered within the scope of the present disclosure.

SUMMARY

A first exemplary embodiment of a disclosed sensor module includes a substrate with a slot formed therein. A sensor is mounted to the substrate and spans the slot. A first cover is disposed on a first side of the substrate and covers at least a portion of the slot. The first cover comprises a first aperture and a second aperture in fluid communication with the slot. The sensor is disposed between the first and second apertures.

A second exemplary embodiment of a disclosed sensor module includes a printed circuit board having a fluid circuit. The fluid circuit has a channel extending through the printed circuit board from an inlet to an outlet. A sensor is operably mounted to the printed circuit board in fluid connection with the fluid circuit.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
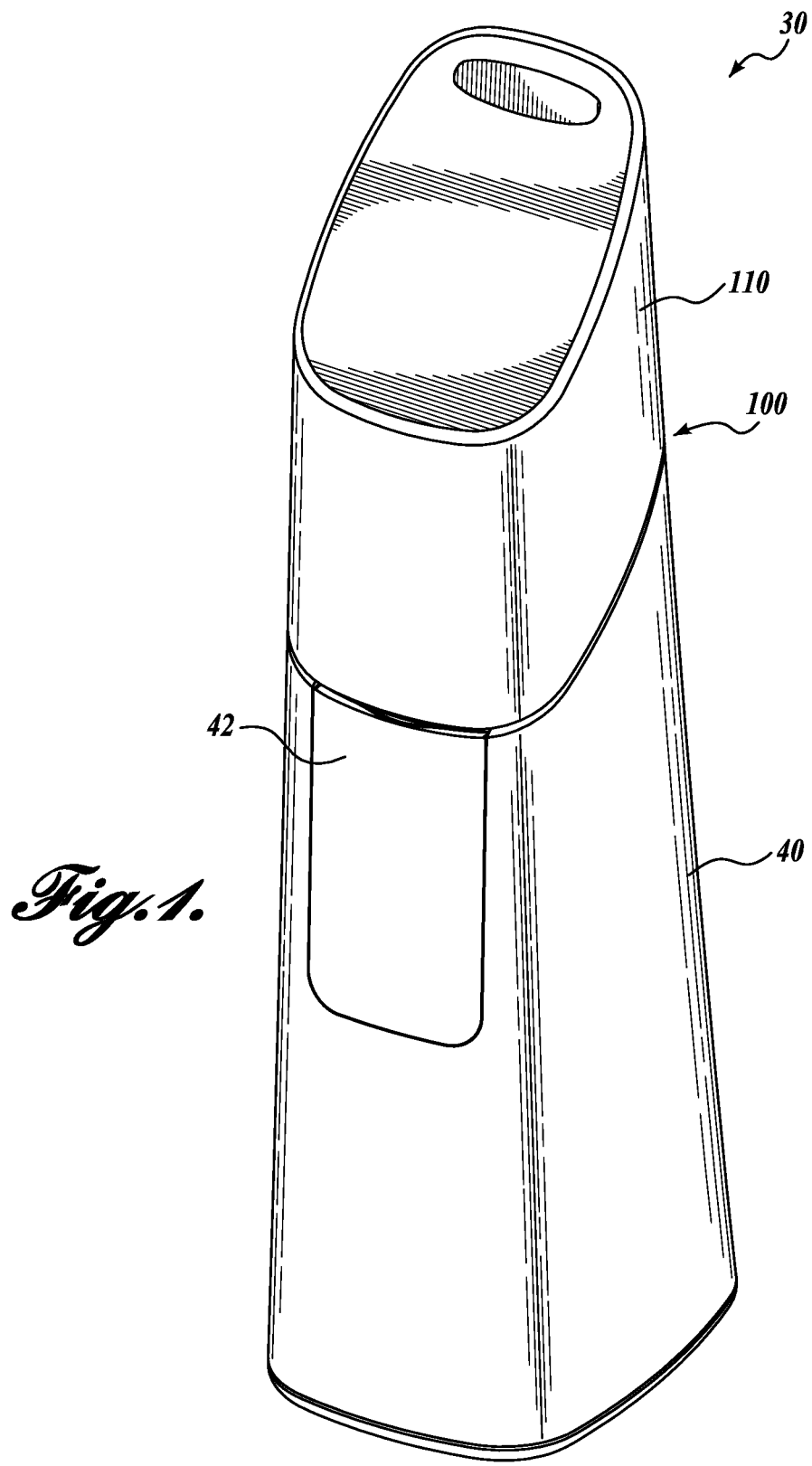
FIG. 1 shows a front isometric view of a breath analysis device with a breath sampling system according to one exemplary embodiment of the present disclosure.
Figure 2:
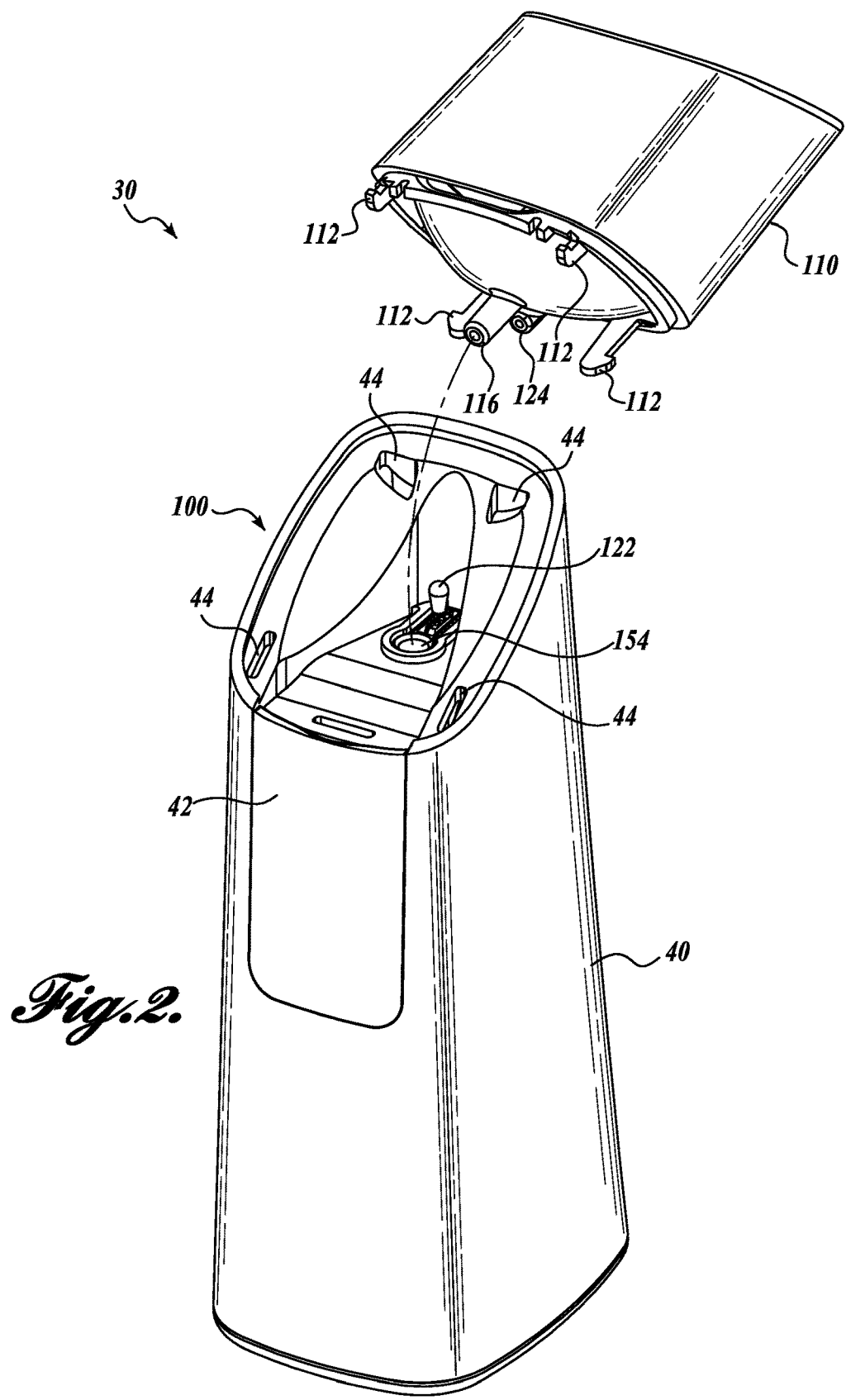
FIG. 2 shows a partially exploded view of the breath sampling system of FIG. 1.

FIGS. 1 and 2 show front and rear isometric views, respectively, of an exemplary embodiment of a breath analysis device 30 that utilizes a breath sampling system 100 according to the present disclosure. The device 30 includes housing 40 that contains the components of the breath analysis device. The housing 40 provides an ergonomic surface that makes the device 30 self-contained and easily portable.

The breath sampling system 100 collects a breath sample from a user and provides it to a sensor module 400 for analysis. The sensor module 400, best shown in FIGS. 13-17, is operatively connected to a processor 60 shown in FIG. 6. As described in further detail below, the processor 60 receives data from the sensor module 400 that can include data related to sensed breath components, breath flow, sensor temperature, and other operating characteristics. In one contemplated embodiment, the processor 60 processes the data and selectively displays information on a display 70 based on the data received from the sensor assembly 400.

In the illustrated embodiment, the display 70 comprises a plurality of lights 72 that can be selectively illuminated to indicate operating conditions, such as state of battery charge, readiness of the device to collect a breath sample, success of a breath sample collection, or any other information that would be desired by the user. The color, display duration, and pattern of the lights can be varied to indicated different conditions. Further, it will be appreciated that disclosed embodiment can incorporate any suitable type of displays and signals to relay information to a user, including LCD screens, LED screens, audible signals, haptic signals, or any other type of combination of displays and signals.

In another contemplated embodiment, the processor 60 stores the data locally, or makes the data available for transfer to a remote storage location or processor, such as a home computer, tablet, smart phone, etc. These and other processor functions suitable for receiving and processing diagnostic data are contemplated and should be considered within the scope of the present disclosure.

Referring now to FIGS. 1-4, the breath sampling system 100 includes a mouthpiece 110 and a pump assembly 140. Generally speaking, a user exhales into the mouthpiece 110 so that the breath flows into a chamber 114 formed in the mouthpiece. The pump assembly 140 then draws a breath sample from the chamber 114 and supplies it to the sensor module 400 for analysis.

As best shown in FIGS. 1 and 2, the mouthpiece is removably coupled to the housing 40. In the illustrated embodiment, a plurality of tabs 112 extend down from the base of the mouthpiece 110 and are received by corresponding slots 44 disposed in the housing 40 to releasably secure the mouthpiece to the housing. It will be appreciated that any number of suitable configurations are possible to secure the mouthpiece to the housing, and such embodiments should be considered within the scope of the present disclosure. Further, embodiments are contemplated wherein the mouthpiece is permanently secured to the housing 40 or integrally formed with the housing.

Figure 3:
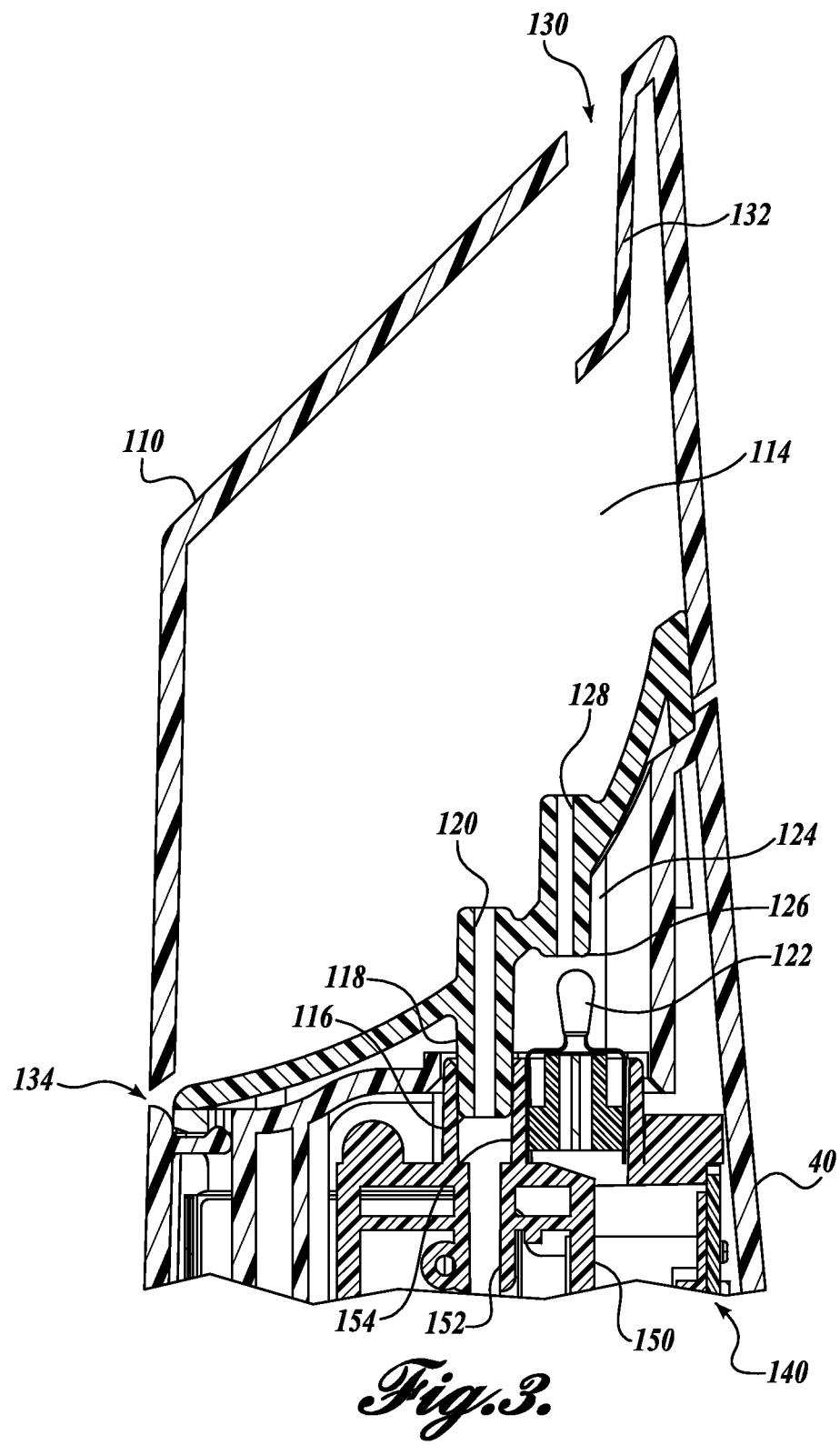
FIG. 3 shows a partial, side cross-sectional view of the breath sampling system of FIG. 1.
Figure 4:
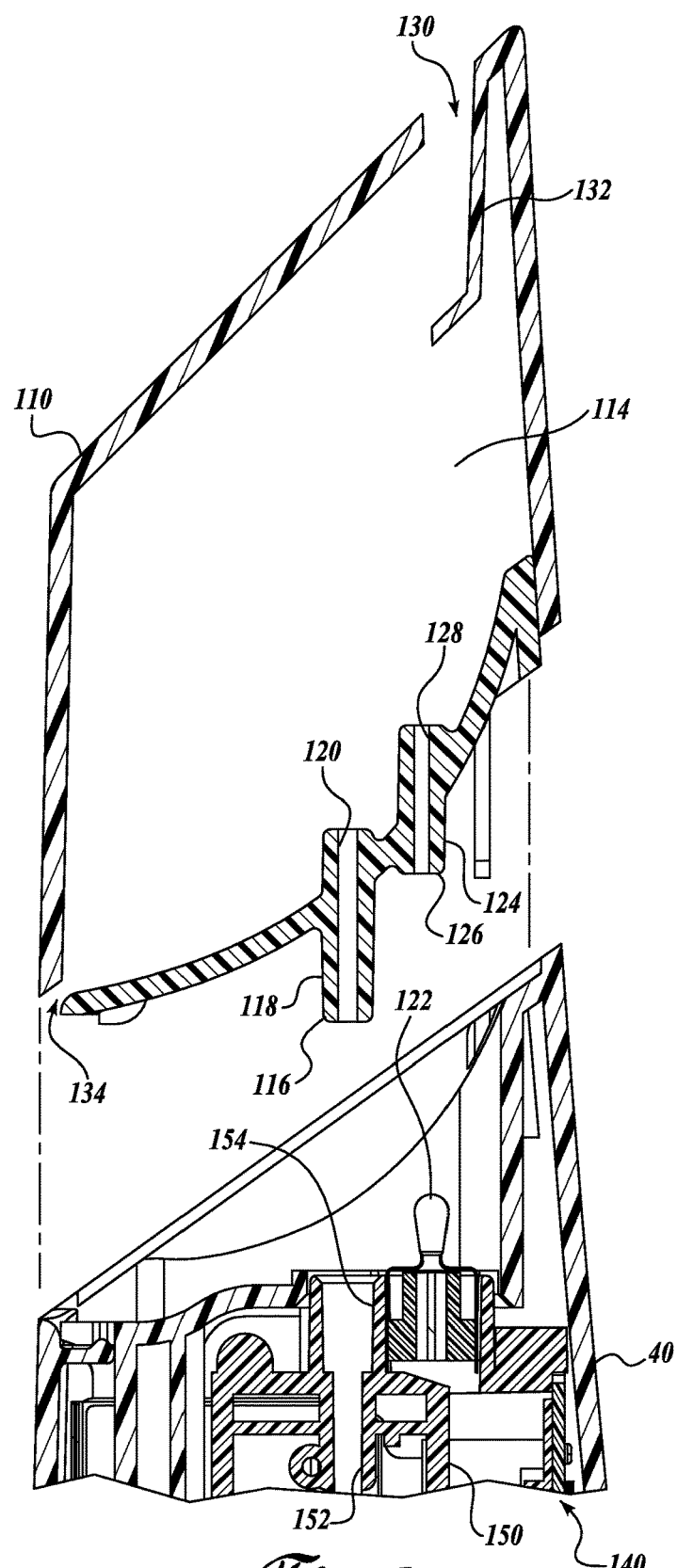
FIG. 4 shows a partially exploded, side cross-sectional view of the breath sampling system of FIG. 1.
Figure 5:
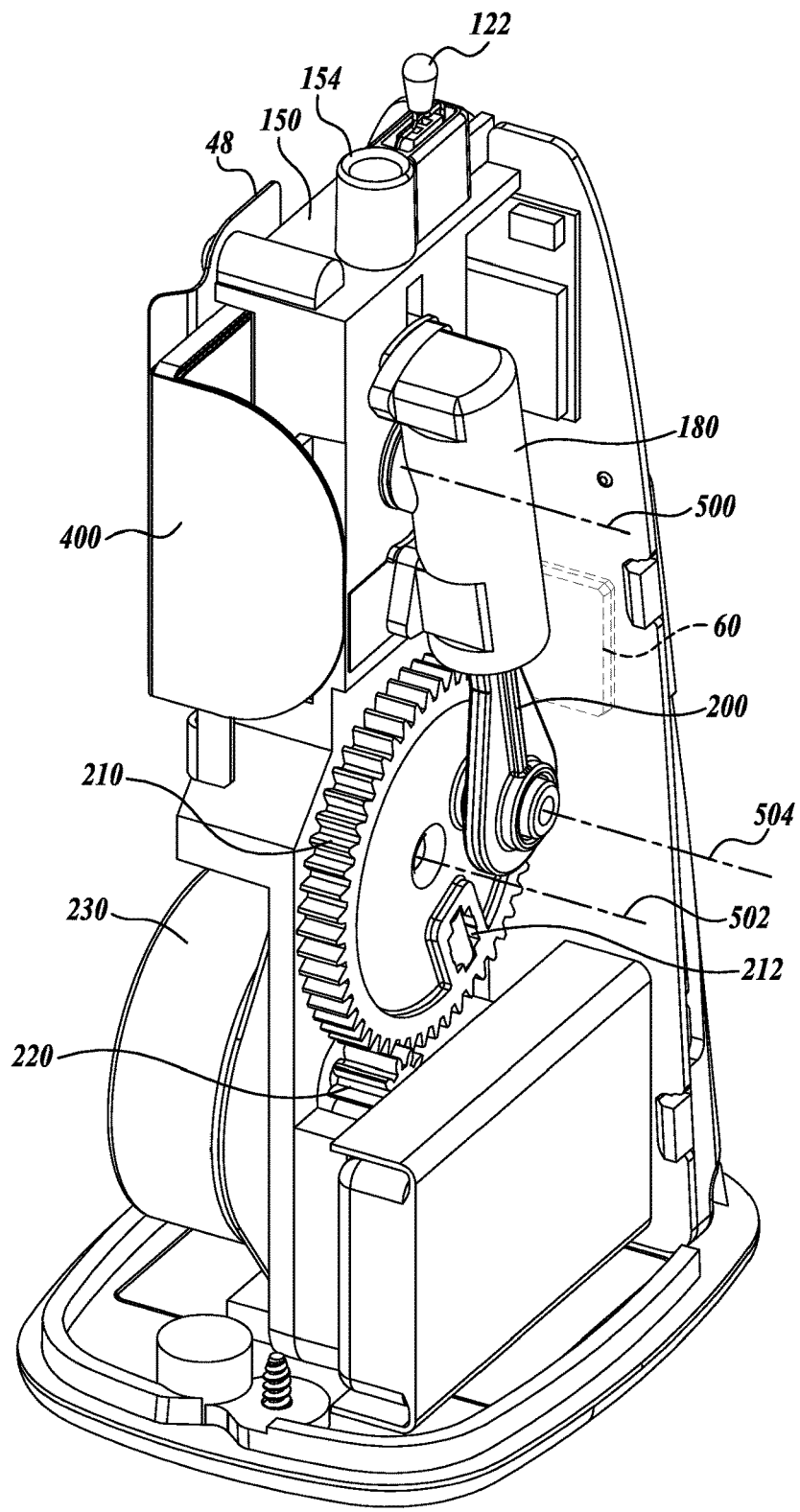
FIG. 5 shows a front isometric view of a pump assembly of the breath sampling system of FIG. 1.

Referring now to FIGS. 2-4, a breath sample port 116 extends downward from a bottom portion of the mouthpiece 110. The breath sample port 116 includes a generally cylindrical body 118 with a central passage 120 extending axially therethrough. The pump assembly 140 includes a manifold located within the housing 40. The manifold 140 has a mouthpiece channel 152 with a mouthpiece channel inlet 154 sized and configured to receive the breath sample port 114. When the mouthpiece 110 is attached to the housing 40, the cylindrical body 118 of the breath sample port 116 extends into the mouthpiece channel inlet 154 so that the chamber 114 of the mouthpiece is in fluid communication with the mouthpiece channel 152.

A breath detection port 124 also extends downward from the bottom portion of the mouthpiece 110. Like the breath sample port 116, the breath detection port 124 includes a cylindrical body 126 with a central passage 128 extending therethrough. The breath sample port 116 is sized and configured so that when the mouthpiece 110 is mounted to the housing 40, the end of the breath sample port is proximate to a breath detection sensor 122. The breath detection sensor 122 is mounted to the pump manifold 150 or another suitable component and is operatively connected to the processor 60.

The disclosed breath detection sensor 122 is preferably a heated glass NTC (negative temperature coefficient) thermistor configured to operate as a hot-wire anemometer. Contemplated alternate embodiments utilize other temperature sensors capable of dissipating heat, such as resistance temperature detectors (RTDs) or PTC (positive temperature coefficient) thermistors. It will be further appreciated that the sensor 122 can also be a pressure sensor, a mass flow sensor, or any other suitable sensor for detecting that breath is being exhaled into the mouthpiece 110. As will be described below, the breath detection sensor senses when a user is breathing into the mouthpiece. Data from the breath detection sensor 122 is received by the processor 60, which determines when a breath suitable for sampling has been introduced into the mouthpiece 110.

The mouthpiece 110 includes an inlet aperture 130 into which a user breathes to introduce a breath sample into the chamber 114 of the mouthpiece. A baffle 132 extends from the edge of the chamber 114 and redirects the breath within the chamber. The baffle controls the introduction of saliva into the chamber 114 and also makes the direction of airflow into the chamber more predictable, thereby providing more consistent breath sample characteristics within the chamber.

The mouthpiece 110 further includes an outlet aperture 134. A typical human exhalation has a volume of approximately 500 ml. The volume of the chamber 114 in the disclosed embodiment is approximately 30 ml. The outlet aperture 134 provides an escape path for excess breath so that a user can provide a longer breath to sample, thereby ensuring that early mouth air is discharged from the chamber 114 or sufficiently diluted with the end tidal air from the airway and lungs. The inlet and outlet apertures 130 and 134 are large enough to allow a user to exhale a breath through the mouthpiece 110, but not so large that the breath becomes significantly diluted by ambient air after the breath is finished.

Referring now to FIGS. 5-10, the pump assembly 140 draws breath from the chamber 114 of the mouthpiece and supplies it to the sensor module 400 in a controlled manner that is consistent and repeatable, thereby improving the accuracy and repeatability of the sensor readings.

The pump assembly 140 includes a cylinder 180 rotatably coupled to the pump manifold 150 about an axis 500. A piston 190 is slidably disposed within the cylinder 180 to define a volume 182 within the cylinder, wherein reciprocating movement of the piston within the cylinder increases and decreases the volume. A drive rod 200 is fixedly secured at one end to the piston 190. A second end of the drive rod is rotatably coupled to a drive gear 210 about an axis 504, which is parallel to axis 500. The drive gear 210 is itself rotatably coupled to the pump manifold 150 or another suitable structure about an axis 502, which is parallel to axes 500 and 504.

A spur gear 220 is rotatably mounted to the pump manifold 150 or other suitable structure about an axis 506. A motor 230 selectively rotates the spur gear 220 about axis 506. The motor 230 is preferably a compact stepper motor; however, it will be appreciated that other motors may be used to selectively rotate the spur gear 220, and such motors should be considered within the scope of the present disclosure.

The spur gear 220 is operatively engaged with the drive gear 210 so that when the motor 230 rotates the spur gear about axis 506, the drive gear 210 rotates about axis 502. A magnet 212 is mounted to the drive gear 210. One or more sensors (not shown), such as a Hall effect sensor, senses the position of the drive gear 210, and sends information about the drive gear position to the processor. It will be appreciated that any number of suitable sensors for sensing the position of the drive gear may be utilized within the scope of the present disclosure.

Figure 8:
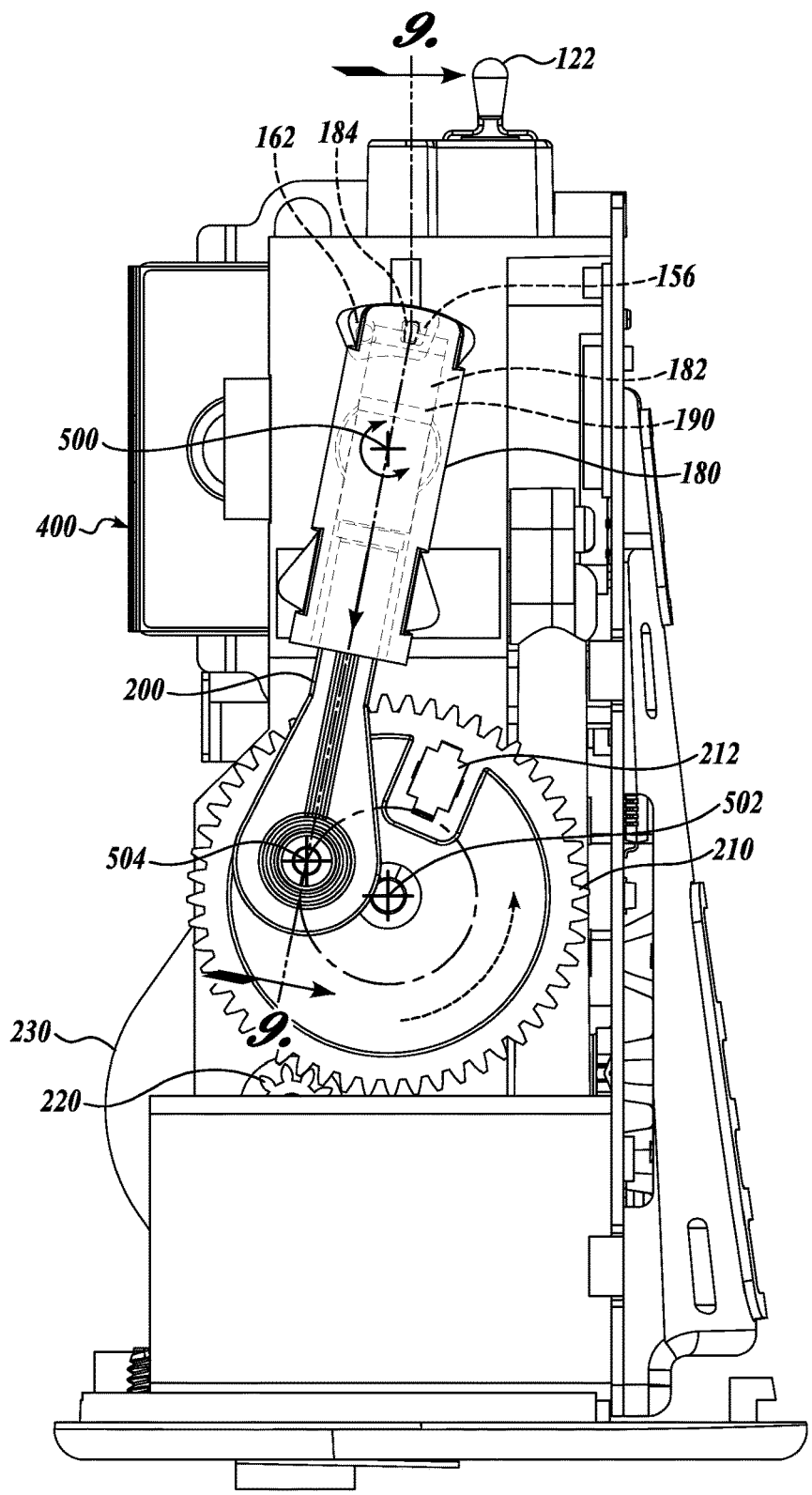
FIG. 8 shows a side view of the pump assembly of FIG. 5 in a first position.
Figure 10:
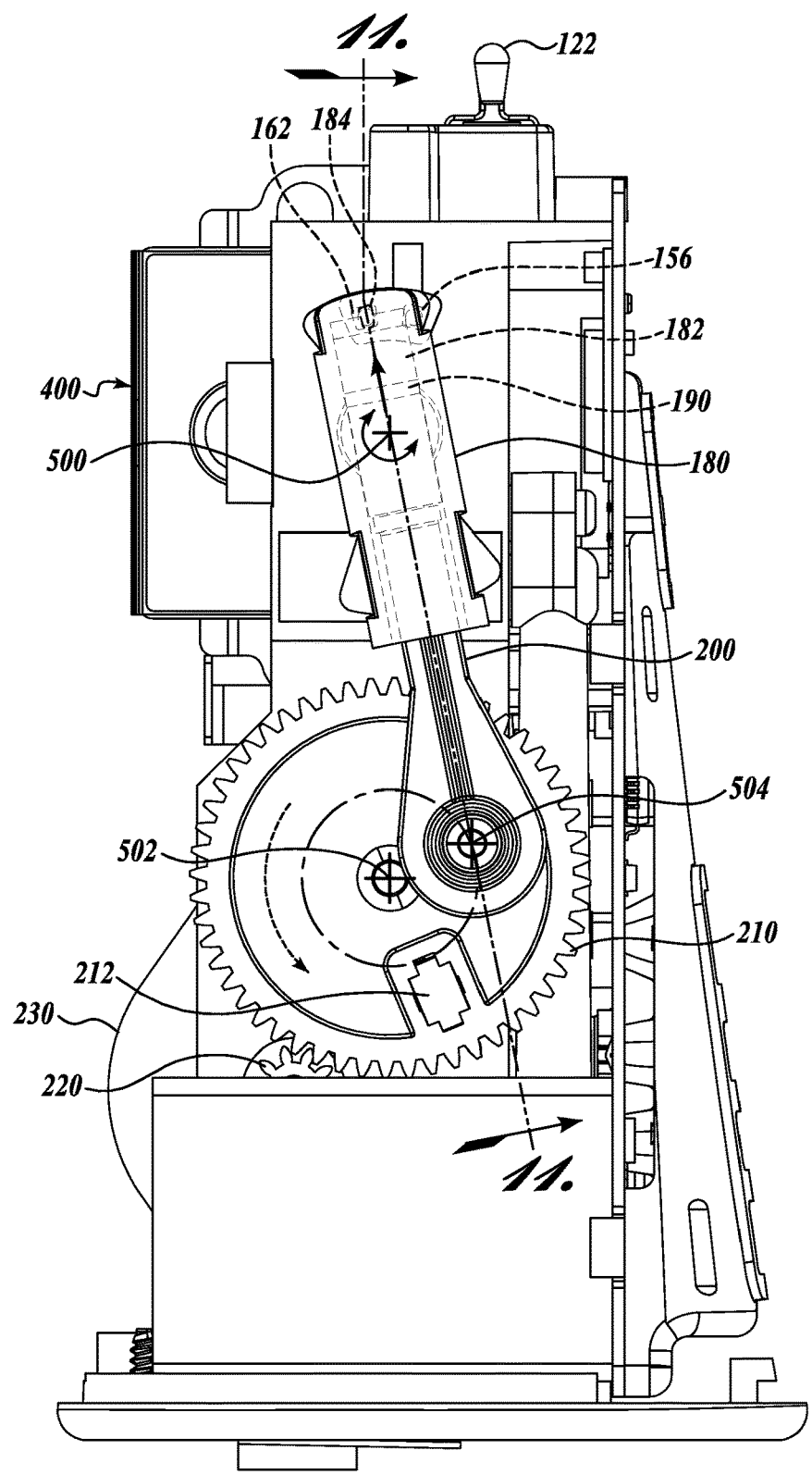
FIG. 10 shows a side view of the pump assembly of FIG. 8 in a second position.

As best shown in FIGS. 8 and 10, rotation of the drive gear 20 reciprocates the drive rod 200 and the piston 190 out of (FIG. 8) and into (FIG. 10) the cylinder 180, increasing and decreasing, respectively, the size of the volume 182 within the cylinder. Because the drive rod 200 is fixedly coupled to the piston 190, rotation of the drive gear 210 also rotates the cylinder 180 back and forth about axis 500.

As the cylinder rotates back and forth about axis 500, a generally planar face 186 formed on the cylinder 180 moves back and forth along an arcuate path in sliding engagement with a face 158 formed on the manifold 150. A channel 184 extends from the interior volume 182 of the cylinder 180 to the cylinder face 158. The cylinder channel 184 moves back and forth with the face 186 to alternately engage a mouthpiece channel outlet 156 and a sensor channel inlet 162, both of which are disposed on the manifold face 158.

Figure 7:
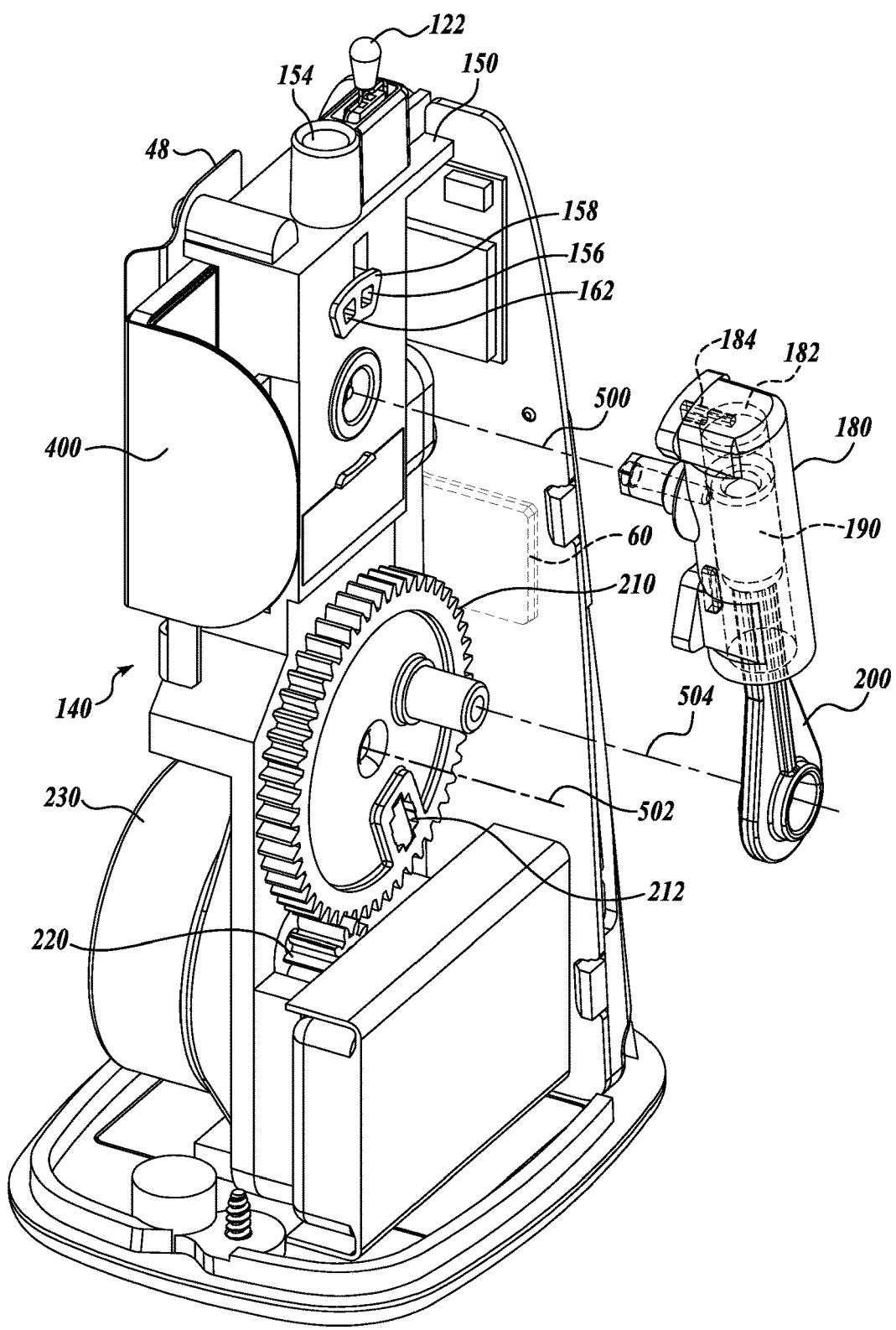
FIG. 7 shows a partially exploded front isometric view of the pump assembly of FIG. 5.

The mouthpiece channel outlet 156 is the end of the previously described mouthpiece channel 152, shown in FIG. 7. When the cylinder 180 is positioned such that the cylinder channel 184 is engaged with the mouthpiece outlet channel 156, the mouthpiece chamber 114 is in fluid connection with the interior volume 182 of the cylinder 180. As best shown in FIG. 8, when the cylinder 180 is so positioned, the drive rod 200 and piston 190 are moving to increase the volume 182 within the cylinder, creating a vacuum that draws gasses from the mouthpiece chamber 114, through the mouthpiece channel 152, and into the interior volume 182 of the cylinder. As this occurs, the sensor channel inlet 160 is covered and sealed by the cylinder face 186.

Figure 11:
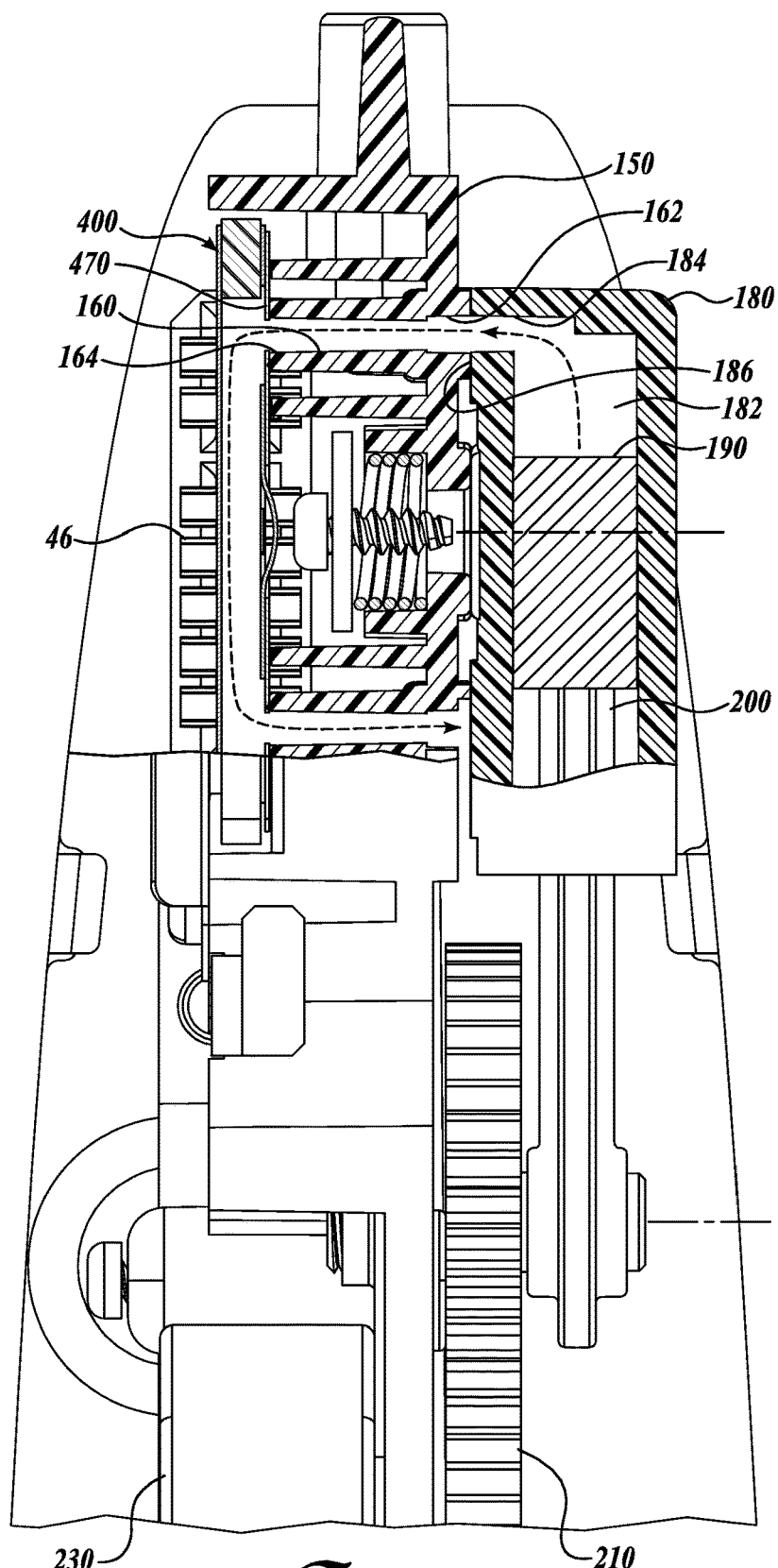
FIG. 11 shows a partial cross-sectional view of the pump assembly of FIG. 10.

As the drive gear 210 continues to rotate, the cylinder 180 rotates so that the cylinder channel 184 disengages with the mouthpiece outlet channel 156, which is then sealed off by engagement with the cylinder face 186. The cylinder channel 184 moves along an arcuate path until it engages the sensor channel inlet 162, as shown in FIGS. 10 and 11. The sensor channel inlet 162 is disposed at one end of a sensor channel 160 formed in the manifold 150. A sensor channel outlet 164 is disposed at a second end of the sensor channel 160 proximate to the sensor module 400. More specifically, the sensor channel outlet 164 is in fluid communication with an inlet 472 to the sensor module 400 so that the sensor channel 160 provides fluid communication between the interior volume 182 of the cylinder 180 and the sensor module inlet 472.

Figure 9:
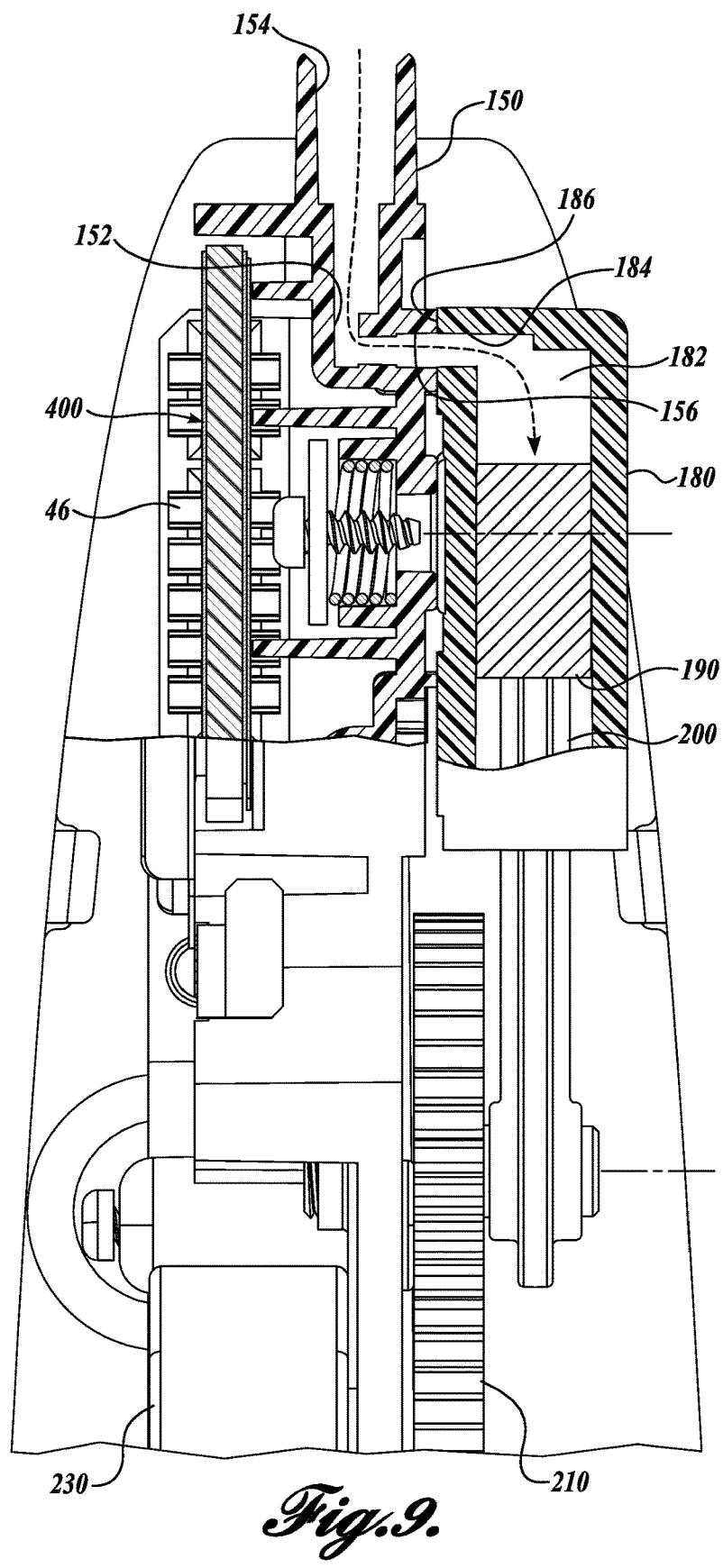
FIG. 9 shows partial cross-sectional view of the pump assembly of FIG. 8.

As best shown in FIG. 9, when the cylinder 180 is positioned so that the sensor channel inlet 162 is engaged with the cylinder channel 184, the drive rod 200 and piston 190 are moving to decrease the volume 182 within the cylinder, thereby increasing the pressure in the cylinder to discharge gasses from the cylinder 180 through the sensor channel 160 and into the sensor module inlet 472. As this occurs, the mouthpiece channel outlet 156 is covered and sealed by the cylinder face 186.

It will be appreciated that the disclosed pump configuration is exemplary only and should not be considered limiting. In this regard, any known pump suitable for selectively providing a breath sample from the mouthpiece chamber 114 to the sensor module 400 can be utilized and should be considered within the scope of the present disclosure.

Figure 12:
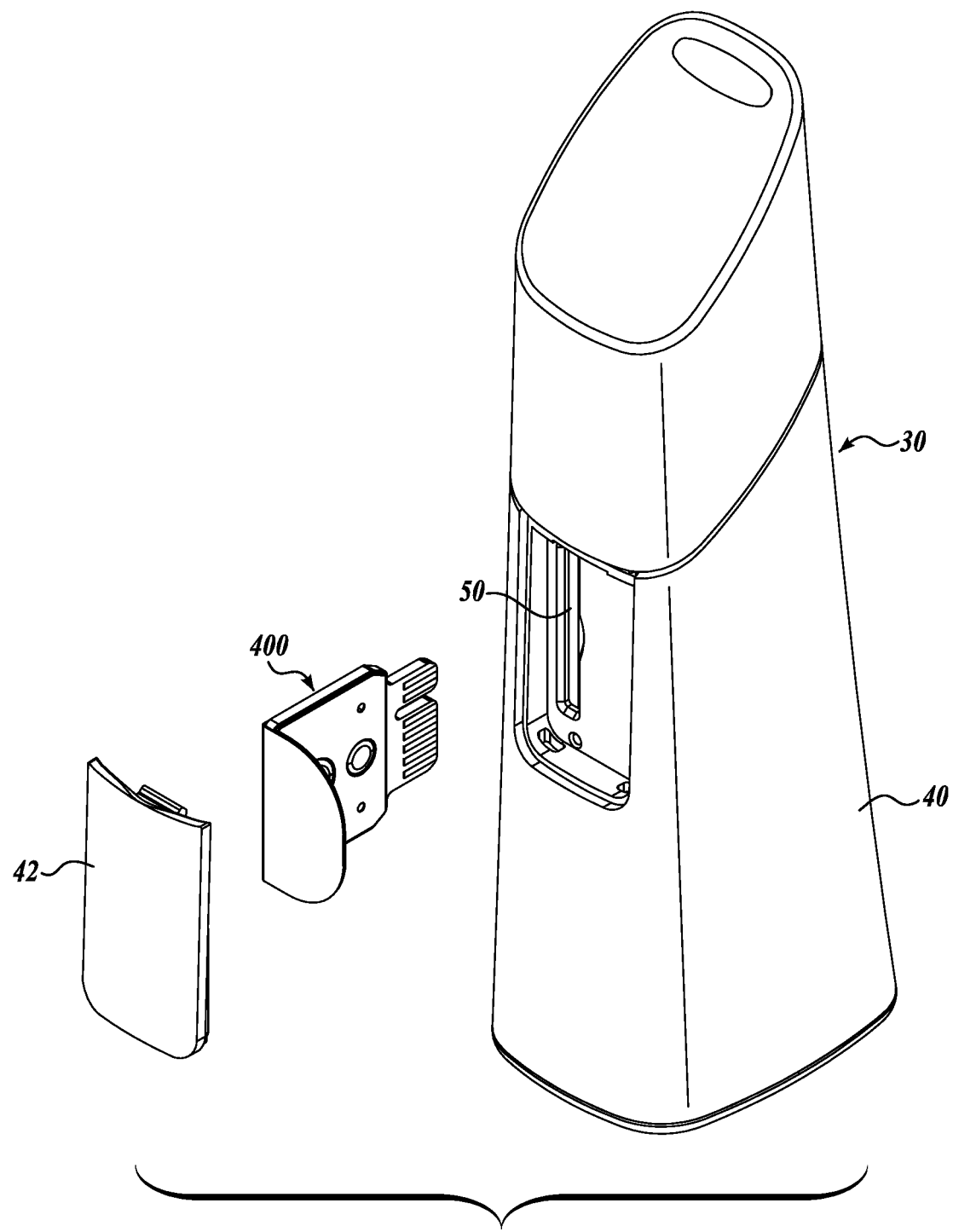
FIG. 12 shows a partially exploded isometric view of the breath analysis device of FIG. 1 with a sensor module removed.

Referring now to FIGS. 12-17, the sensor module 400 will now be described. The presently disclosed sensor module 400 is preferably mounted to the breath analysis device 30 without the use of fasteners, welds, adhesives, etc., so that the sensor module can be easily removed and replaced. As shown in FIG. 12, the illustrated embodiment of the breath analysis device 30 includes a removable cover 42 releasably secured to the housing 40 to cover a slot 50. As will be described in further detail, replacing a sensor module 400 is accomplished by removing the cover 42, pulling on the sensor module to disengage the sensor module from the breath analysis device 30, inserting a replacement sensor module into the slot 50 with enough pressure to seat the sensor module, and reattaching the cover. It will be appreciated, however, that the sensor module need not be removable, and alternate embodiments utilizing various permanent and non-permanent mounting configurations are contemplated.

Figure 13:
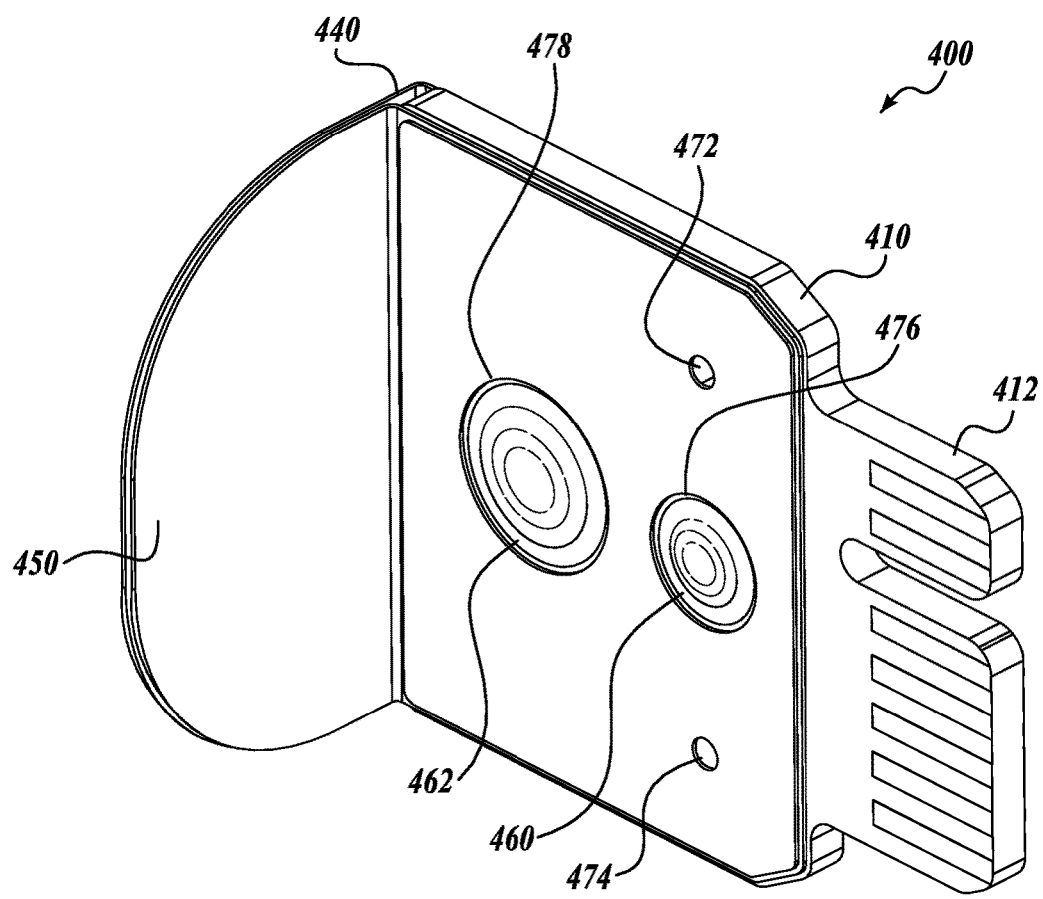
FIG. 13 shows an isometric view of the sensor module of FIG. 12 according to one exemplary embodiment of the present disclosure.
Figure 14:
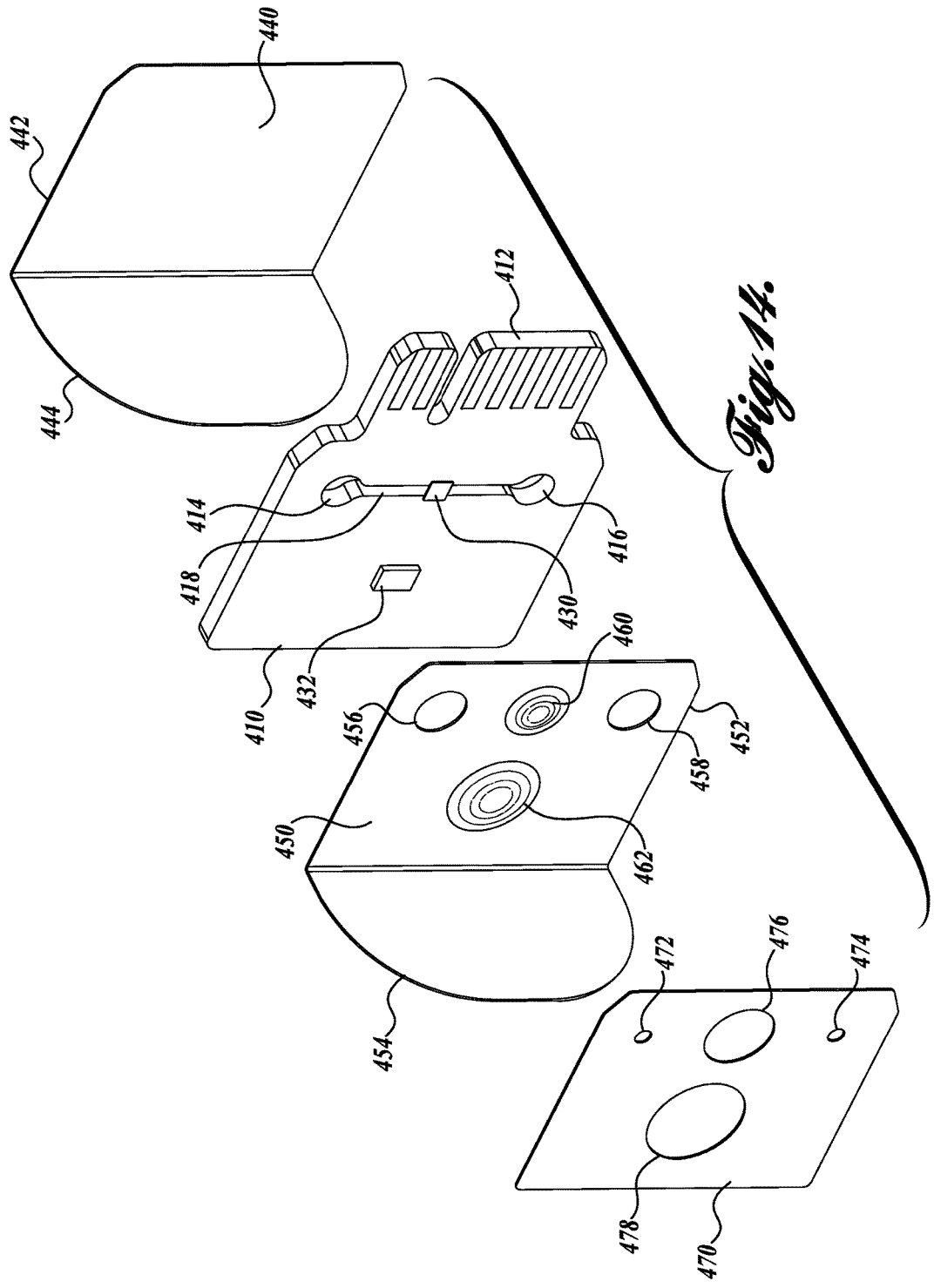
FIG. 14 shows a partially exploded isometric view of the sensor module of FIG. 13.
Figure 15:
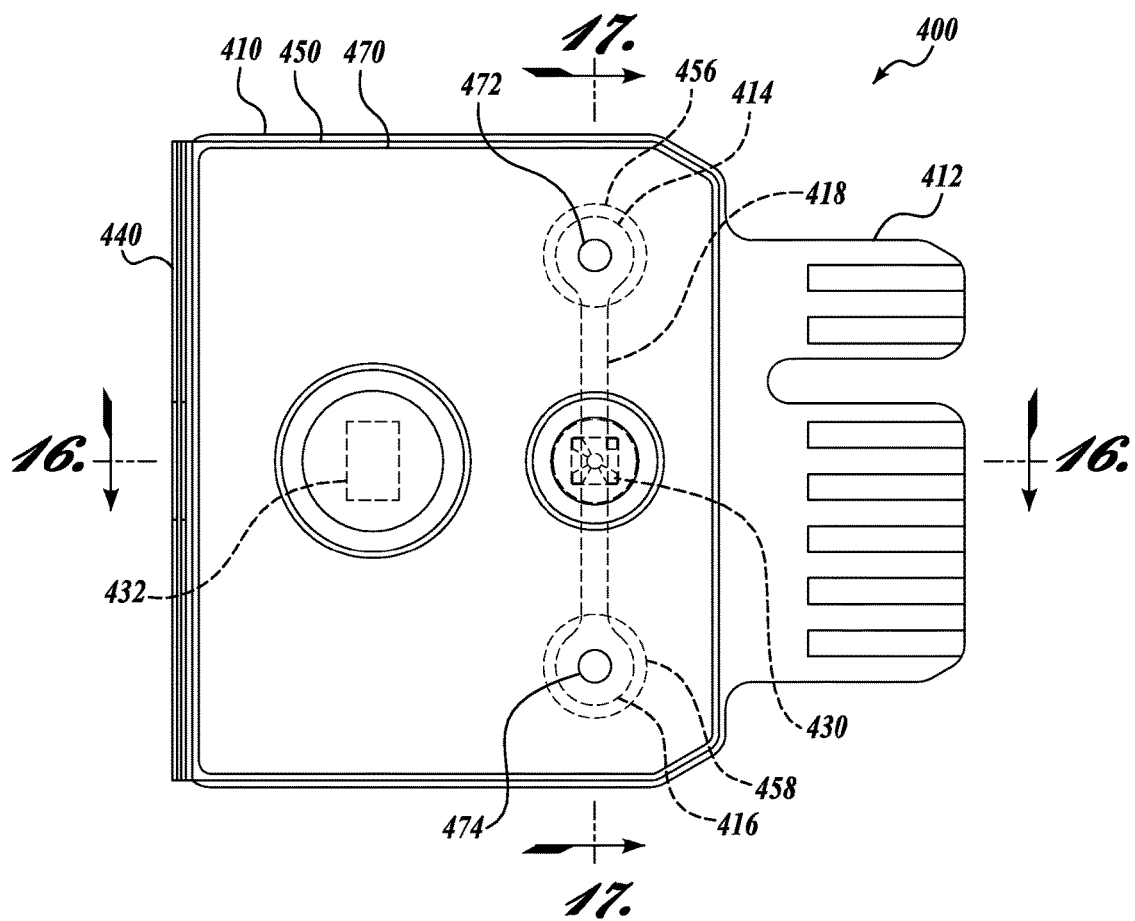
FIG. 15 shows a side view of the sensor module of FIG. 13.

As shown in FIGS. 13 and 14, the illustrated embodiment of a sensor module 400 includes a printed circuit board 410 (PCB) disposed between a first cover 440 and a second cover 450. The PCB 410 has an edge connector 412 sized and configured to be releasably coupled to a socket 46, shown in FIGS. 6 and 11. The socket 46 is operably connected with the processor 60 so that data can be sent between the PCB 410 and the processor. As best shown in FIG. 14, a first hole 414 and a second hole 416 are formed in the PCB 410. A slot 418 extends between the first and second hole 414 and 416. Although the holes 414 and 416 and slot 418 are illustrated as extending through the PCB 410, alternate embodiments are contemplated in which one or more of these features extends only partially through the PCB.

An acetone sensor 430 is mounted to the PCB 410 so that the sensor spans the slot 418 formed in the PCB. In the illustrated embodiment, the sensor 430 is flat tungsten trioxide ($WO_3$) disposed on an alumina or anodic aluminum oxide (AAO) substrate. The described sensor 430 is suitable for detecting acetone in a breath sample; however, it is contemplated that other sensors suitable for sensing acetone may also be used. Further, sensors useful for sensing the presence, level, or other characteristics of other sample components may be utilized, and such sensors should be considered within the scope of the present disclosure.

A memory chip 432 is optionally mounted to the PCB 410. In the illustrated embodiment, the memory chip 432 is an EEPROM that is programmed with sensor 430 parameters, authentication data, and other information to be communicated with the processor 60. It will be appreciated that any number of other components may be mounted to the PCB 410 to provide functionality to the sensor module 400 and the breath analysis device 30 as a whole.

A first cover 440 is made of foil or another suitable material and has a generally L-shaped profile. In this respect, the first cover 440 has a first portion 442 corresponding to the PCB 410 and a second portion 444 extending approximately 90° from the first portion 442. A second cover 450 is similar to the first cover 440, being made of foil or another suitable material and having a generally L-shaped profile. The second cover 450 further includes a first aperture 456 and a second aperture 458 extending therethrough and positioned to correspond to the first and second holes 414 and 416, respectively, in the PCB 410. The second cover 450 further includes a first dimple 460 and a second dimple 462 that are sized and positioned to correspond to the acetone sensor 430 and the memory chip 432, respectively.

Figure 16:
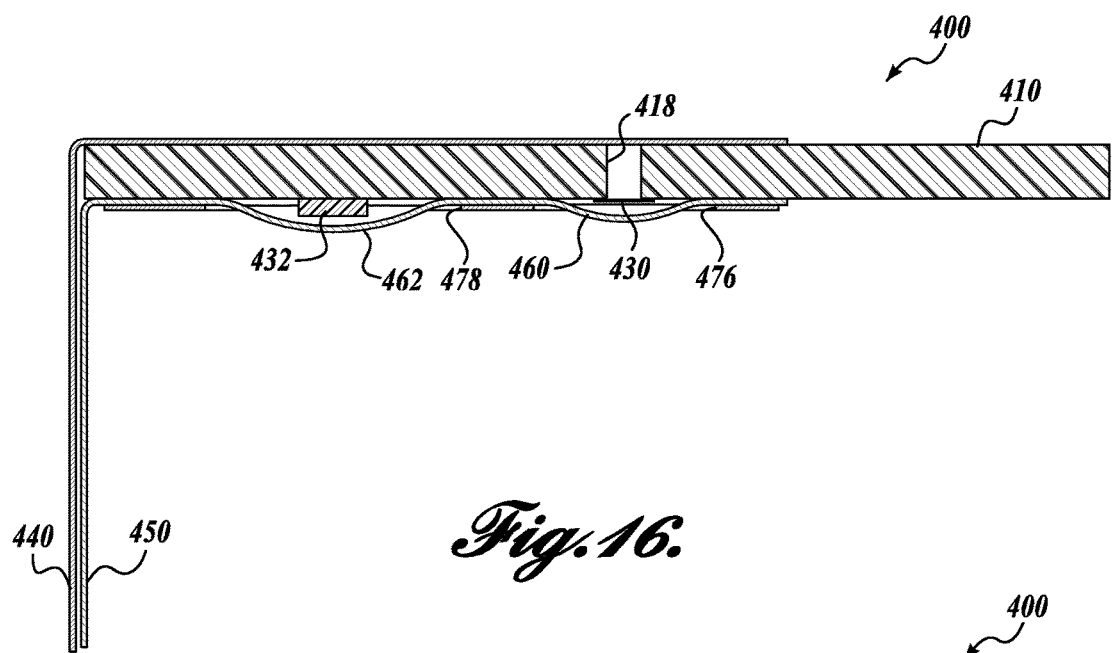
FIG. 16 shows a first cross-sectional view of the sensor module of FIG. 13.
Figure 17:
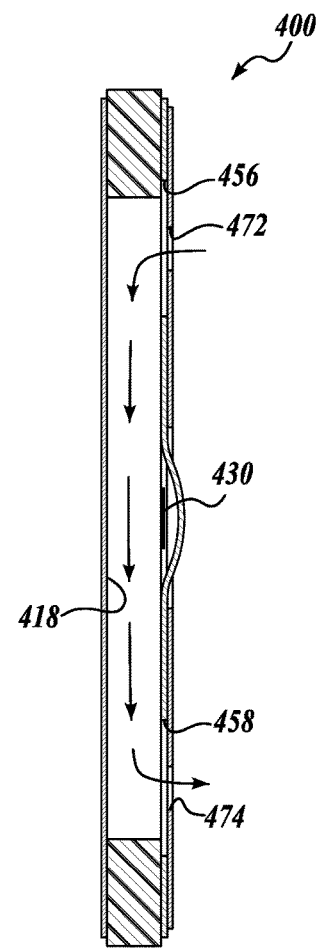
FIG. 17 shows a second cross-sectional view of the sensor module of FIG. 13.
Figure 18:
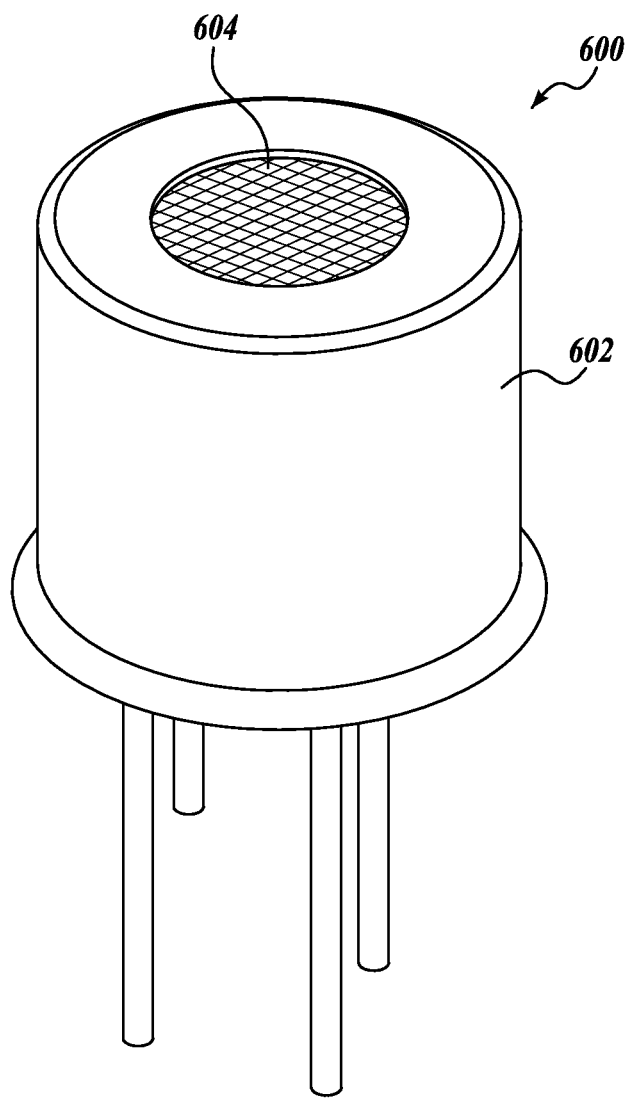
FIG. 18 shows an isometric view of a known breath acetone sensor.

As shown in FIGS. 13 and 15-17, the sensor module 400 is assembled so that the PCB 410 is disposed between the first cover 440 and the second cover 450. The first portion 442 of the first cover 440 covers one side of the PCB 410, including the holes 414 and 416 and the slot 418. Similar to the first cover 440, the first portion 452 of the second cover 450 covers the other side of the PCB 410, including the holes 414 and 416 and the slot 418. The first and second apertures 456 and 458 of the second cover 450 are aligned with the first and second holes 414 and 418, respectively, of the PCB 410. As shown in FIG. 17, the PCB 410 cooperates with the first and second covers 440 and 450 to form pneumatic circuit defined from the first aperture 456, through the slot 418, and out the second aperture 458. As best shown in FIG. 16, the first and second dimples 460 and 462 are positioned to provide clearance between the second cover 450 and the acetone sensor 430 and the memory chip 432, respectively.

The illustrated embodiment also includes a protective cover 470 positioned over the second cover 450 so that the second cover is disposed between the protective cover 470 and the PCB 410. The protective cover 470 is shaped approximately like the first portion 452 of the second cover 450 and has apertures 472 and 474 that correspond to the first and second apertures 456 and 458, respectively, of the second cover. The protective cover 470 also has third and fourth apertures 476 and 478 that correspond to and provide clearance for the first and second dimples 460 and 462, respectively. The protective cover 470 protects the second cover 450 which would otherwise be susceptible to tearing, particularly around the first and second apertures 456 and 458. As such, the protective cover 470 is preferably made from a material having suitable strength and durability, such as a metal or polymeric material.

Figure 6:
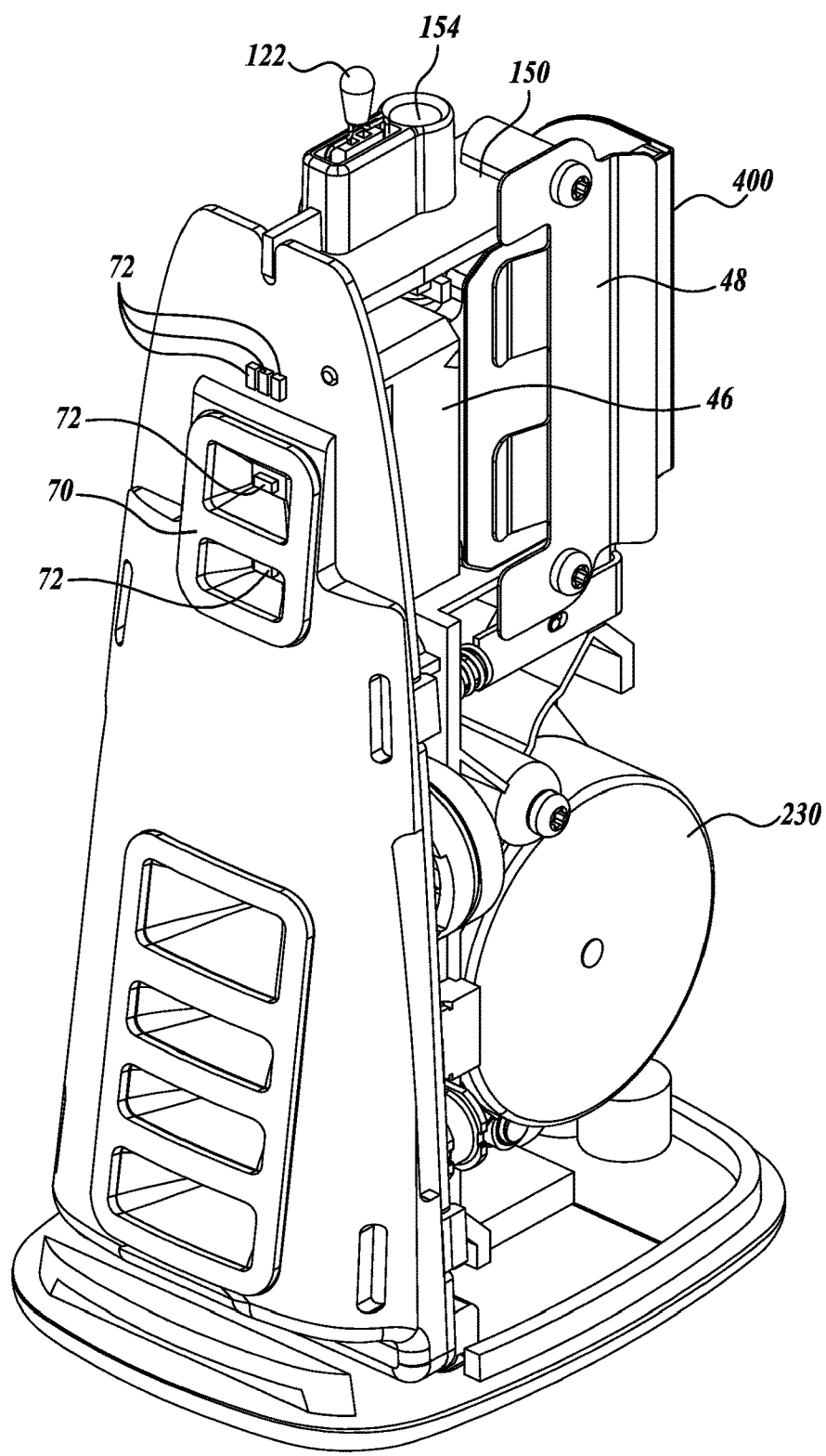
FIG. 6 shows a rear isometric view of the pump assembly of FIG. 5.

As shown in FIGS. 12 and 13, the second portion 444 of the first cover 440 and the second portion 454 of the second cover 450 extend laterally from an edge of the PCB 410 opposite the edge connector 412 to form a handle that facilitates insertion and removal of the sensor module 400. Referring to FIG. 12, to replace a sensor module 400, a user removes the cover 42 and, pulls on the sensor module to remove the module from the socket 46. A new sensor module 400 is then inserted in the slot 50 until the edge connector 412 of the new sensor module is seated in the socket 46. As best shown in FIG. 6, an optional spring clip 40 helps retain the sensor module 400 within the socket 46. Known sensors are susceptible to a buildup of contaminants and/or interferents, which can negatively impact the accuracy of the sensor. Thus, a sensor module 400 that is easily replaceable by a user provides an advantage over known sensors.

A method for collecting and sampling breath using the previously described breath analysis device 30 will now be described. To begin, a user places his or her mouth over the inlet aperture 130 of the mouthpiece 110 and exhales. Referring to FIG. 3, the exhaled breath is deflected off of the baffle 132 and circulates around the mouthpiece chamber 114. As the user continues to exhale, a portion of the breath escapes through the outlet aperture 134, and a portion of the breath escapes through the breath detection port 124. The pump assembly 140 is in the position shown in FIG. 10, so the mouthpiece channel 152 is sealed by the cylinder face 186, and none of the breath sample passes into the cylinder 180.

The breath passing through the breath detection port 124 passes over the breath detection sensor 122, which senses that a breath is being exhaled into the mouthpiece 110. When exhalation has been sensed for a predetermined amount, the breath detection sensor 122, which is operably associated with the processor 60 sends data to the processor indicating that an adequate sample has been collected. By having a user exhale into the mouthpiece 110 for a predetermined amount of time, it is assured that the breath sample within the mouthpiece chamber 114 is end tidal air, which yields more accurate readings.

The processor 60 controls the display to indicate to the user to stop exhaling into the mouthpiece 110. It will be appreciated that the signal need not be visual, as indicated in the exemplary embodiment, but can be audible, haptic, or any other type or combination of signals.

Next, the pump assembly 140 works to provide the breath sample from the mouthpiece chamber 114 to the acetone sensor 430 in a controlled, repeatable manner. Referring to FIGS. 8 and 10, the motor 230 rotates the drive gear 210 in a counterclockwise direction. As a result, the cylinder 180 rotates back and forth about axis 500. When the cylinder 180 is in the position shown in FIG. 8, the cylinder channel 184 is in fluid communication with the mouthpiece chamber 114, and the piston 190 is moving downward in the cylinder. As a result, a portion of the breath sample is drawn from the mouthpiece chamber 114 into the volume 182 of the cylinder 180, as shown in FIG. 9. Continued rotation of the drive gear 210 rotates the cylinder 180 about axis 500 to the position shown in FIG. 10, wherein the cylinder channel 184 is in fluid communication with the sensor channel 160. The rotation of the drive gear 210 moves the piston 190 upward in the cylinder 180, driving the breath sample from the cylinder volume 182 out through the sensor channel 160, as shown in FIG. 11.

It will be appreciated that the disclosed configuration allows the flow rate of the breath sample to the sensor module 400 to be controlled. In the disclosed embodiment, the preferred flow rate is in the range of 5 ml/min.-100 ml/min. It will be appreciated, however, that the motor 230, which is controlled by the processor 60, can increase the rotational speed of the drive gear 210 to increase the flow rate or decrease the rotational speed of the drive gear to decrease the flow rate. Thus, the flow rate can be tailored to provide optimal accuracy for a particular sensor type or application.

Still referring to FIG. 11, the breath sample is discharged from the sensor channel 160 into the inlet (aperture 472) of the sensor module 400. When installed, the protective cover 470 of the sensor module 400 preferably contacts a portion of the manifold 150 so that the connection between the sensor channel 160 and aperture 473 is sealed. In this manner, the breath sample can flow through aperture 472 into the slot 418 in the sensor module 400 with no loss of the sample. It will be appreciated that other sealing configurations are possible and that some loss of the breath sample can be acceptable, provided that the accuracy and repeatability of the readings is not impacted too greatly.

The breath sample passes through the slot 418 where it flows over the acetone sensor 430 and then out the sensor module outlet (aperture 474). The motor 230 continues to rotate the drive gear 212 until a suitable breath sample has been passed over the acetone sensor 430. It will be appreciated that the speed and duration of the pump assembly 140 operation can be varied to provide optimum exposure of the particular sensor contained within the sensor module 430.

When the analysis of the breath sample is completed, the motor 230 reverses direction, and rotates the drive gear 210 in a clockwise direction. Reversing the rotation of the drive gear 210 reverses the direction of flow through the pump assembly 140. Accordingly, ambient air is drawn into the sensor module outlet, through the sensor module 400 and sensor channel 160 into the cylinder 180. The ambient air is then discharged into the mouthpiece 110 and out the inlet aperture 130 and outlet aperture 124. In this manner, the breath sample is purged from the sensor module 400 and the mouthpiece 110, ensuring that one breath sample will not influence the results of the next breath sample.

While illustrative embodiments have been illustrated and described, it will be appreciated that various changes can be made therein without departing from the spirit and scope of the invention.

The embodiments of the invention in which an exclusive property or privilege is claimed are defined as follows:

1. A sensor module configured to be detachably mounted to a mount of a sensing device, the sensor module comprising:
   (a) a substrate having a slot formed therein, the substrate comprising an edge connector formed on an edge of the substrate, the edge connector being configured to detachably couple the substrate to the mount of the sensing device;
   (b) a sensor mounted to the substrate and spanning the slot; and
   (c) a first cover disposed on a first side of the substrate and covering at least a portion of the slot, the first cover comprising a first aperture and a second aperture in fluid communication with the slot, wherein the sensor is disposed between the first and second apertures.

2. The sensor module of claim 1, wherein the slot extends only partially through the substrate from the first side of the substrate.

3. The sensor module of claim 1, wherein at least a portion of the slot extends through a second side of the substrate.

4. The sensor module of claim 3, further comprising a second cover disposed on the second side of the substrate, the second cover covering the slot.

5. The sensor module of claim 1, wherein the sensor is disposed under a dimple formed in the first cover.

6. The sensor module of claim 1, wherein the sensor is an acetone sensor.

7. The sensor module of claim 1, wherein the sensor comprises $WO_3$.

8. The sensor module of claim 1, wherein the substrate is a printed circuit board.

* * * * *